United States Patent
Onuma et al.

(10) Patent No.: US 9,775,637 B2
(45) Date of Patent: Oct. 3, 2017

(54) PROBE UNIT, TREATMENT INSTRUMENT, AND TREATMENT SYSTEM

(71) Applicant: OLYMPUS CORPORATION, Tokyo (JP)

(72) Inventors: Chie Onuma, Fuchu (JP); Manabu Ishikawa, Hachioji (JP); Koki Tokunaga, Kokubunji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/011,566

(22) Filed: Jan. 31, 2016

(65) Prior Publication Data

US 2016/0151647 A1    Jun. 2, 2016

Related U.S. Application Data

(63) Continuation of application No. PCT/JP2014/054466, filed on Feb. 25, 2014.

(Continued)

(51) Int. Cl.
*A61B 17/32* (2006.01)
*A61B 17/16* (2006.01)
(Continued)

(52) U.S. Cl.
CPC ........ *A61B 17/320068* (2013.01); *A61B 1/32* (2013.01); *A61B 17/025* (2013.01);
(Continued)

(58) Field of Classification Search
CPC . A61B 1/32; A61B 17/025; A61B 2017/0256; A61B 2017/0268;
(Continued)

(56) References Cited

U.S. PATENT DOCUMENTS

| 4,545,374 A | 10/1985 | Jacobson |
| 5,331,975 A | 7/1994 | Bonutti |

(Continued)

FOREIGN PATENT DOCUMENTS

| EP | 2464417 A2 | 6/2012 |
| JP | H03-146047 A | 6/1991 |

(Continued)

OTHER PUBLICATIONS

Apr. 28, 2014 International Search Report issued in International Patent Application No. PCT/JP2014/054466.
(Continued)

*Primary Examiner* — Larry E Waggle, Jr.
(74) *Attorney, Agent, or Firm* — Oliff PLC

(57) ABSTRACT

A probe unit includes, a probe configured to treat a bone by ultrasonic vibration, a hollow sheath which surrounds the probe and which has a first portion at a small distance from a central axis, and a second portion at a greater distance from the central axis than the first portion, and a knob configured to rotate the sheath relative to the probe between a first position for insertion between the bone and a living tissue facing the bone so that the first portion is located between the bone and the living tissue and a second position for insertion between the bone and the living tissue so that the second portion is located between the bone and the living tissue.

3 Claims, 10 Drawing Sheets

Related U.S. Application Data

(60) Provisional application No. 61/883,520, filed on Sep. 27, 2013.

(51) Int. Cl.

| | |
|---|---|
| *A61C 1/07* | (2006.01) |
| *A61B 1/32* | (2006.01) |
| *A61B 17/17* | (2006.01) |
| *A61B 17/22* | (2006.01) |
| *A61M 29/00* | (2006.01) |
| *A61B 17/02* | (2006.01) |
| *A61B 17/3211* | (2006.01) |
| *A61N 7/00* | (2006.01) |
| *A61B 90/00* | (2016.01) |
| *A61B 17/34* | (2006.01) |
| *A61B 17/00* | (2006.01) |
| *A61B 17/29* | (2006.01) |

(52) U.S. Cl.
CPC .......... *A61B 17/16* (2013.01); *A61B 17/1604* (2013.01); *A61B 17/1613* (2013.01); *A61B 17/1628* (2013.01); *A61B 17/1633* (2013.01); *A61B 17/1657* (2013.01); *A61B 17/1659* (2013.01); *A61B 17/17* (2013.01); *A61B 17/1732* (2013.01); *A61B 17/1735* (2013.01); *A61B 17/22* (2013.01); *A61B 17/22004* (2013.01); *A61B 17/32* (2013.01); *A61B 17/3211* (2013.01); *A61B 90/361* (2016.02); *A61B 90/37* (2016.02); *A61C 1/07* (2013.01); *A61M 29/00* (2013.01); *A61N 7/00* (2013.01); *A61B 2017/00398* (2013.01); *A61B 2017/0256* (2013.01); *A61B 2017/0268* (2013.01); *A61B 2017/0275* (2013.01); *A61B 2017/22005* (2013.01); *A61B 2017/22011* (2013.01); *A61B 2017/2929* (2013.01); *A61B 2017/320028* (2013.01); *A61B 2017/320052* (2013.01); *A61B 2017/320072* (2013.01); *A61B 2017/348* (2013.01); *A61B 2017/3482* (2013.01); *A61B 2017/3484* (2013.01); *A61B 2017/3486* (2013.01)

(58) Field of Classification Search
CPC ............ A61B 2017/0275; A61B 17/16; A61B 17/1604; A61B 17/1613; A61B 17/1628; A61B 17/1633; A61B 17/1657; A61B 17/1659; A61B 17/17; A61B 17/1732; A61B 17/1735; A61B 17/22; A61B 17/22004; A61B 2017/22005; A61B 2017/22011; A61B 17/32; A61B 17/320068; A61B 2017/320072; A61B 2017/348; A61B 2017/3482; A61B 2017/3484; A61B 2017/3486; A61B 2017/320052; A61B 2017/320068; A61C 1/07; A61M 29/00

See application file for complete search history.

(56) References Cited

U.S. PATENT DOCUMENTS

| | | |
|---|---|---|
| 5,342,384 A | 8/1994 | Sugarbaker |
| 5,391,144 A | 2/1995 | Sakurai et al. |
| 5,906,628 A | 5/1999 | Miyawaki et al. |
| 2004/0181273 A1* | 9/2004 | Brasington .......... A61M 29/02 623/1.15 |
| 2005/0033201 A1 | 2/2005 | Takahashi et al. |
| 2005/0209627 A1 | 9/2005 | Kick et al. |
| 2006/0111739 A1* | 5/2006 | Staufer ............ A61B 17/00234 606/192 |
| 2007/0038157 A1 | 2/2007 | Yamada et al. |
| 2010/0191173 A1* | 7/2010 | Kimura ............ A61B 17/32006 604/21 |
| 2010/0318028 A1 | 12/2010 | Tsuang et al. |
| 2011/0034775 A1* | 2/2011 | Lozman ............ A61B 17/1684 600/204 |
| 2011/0040212 A1 | 2/2011 | Dietz et al. |
| 2011/0196286 A1 | 8/2011 | Robertson et al. |
| 2011/0270295 A1* | 11/2011 | Litvack ............ A61B 17/0218 606/192 |
| 2012/0095472 A1 | 4/2012 | Young |
| 2012/0130192 A1 | 5/2012 | Rasmussen et al. |

FOREIGN PATENT DOCUMENTS

| | | | |
|---|---|---|---|
| JP | 2008-119250 | A | 5/2008 |
| JP | 2011-524209 | A | 9/2011 |
| WO | 2007/046860 | A2 | 4/2007 |
| WO | 2009/024729 | A2 | 2/2009 |
| WO | 2009/152470 | A1 | 12/2009 |
| WO | 2010/087060 | A1 | 8/2010 |
| WO | 2010/123825 | A1 | 10/2010 |

OTHER PUBLICATIONS

Jun. 30, 2015 Office Action issued in Japanese Patent Application No. 2015-516304.
Apr. 18, 2017 Search Report issued in European Patent Application No. 14850013.5.
Jul. 7, 2017 Office Action issued in Chinese Patent Application No. 201480053224.7.
Jun. 9, 2017 Office Action issued in European Patent Application No. 14847518.9.

\* cited by examiner

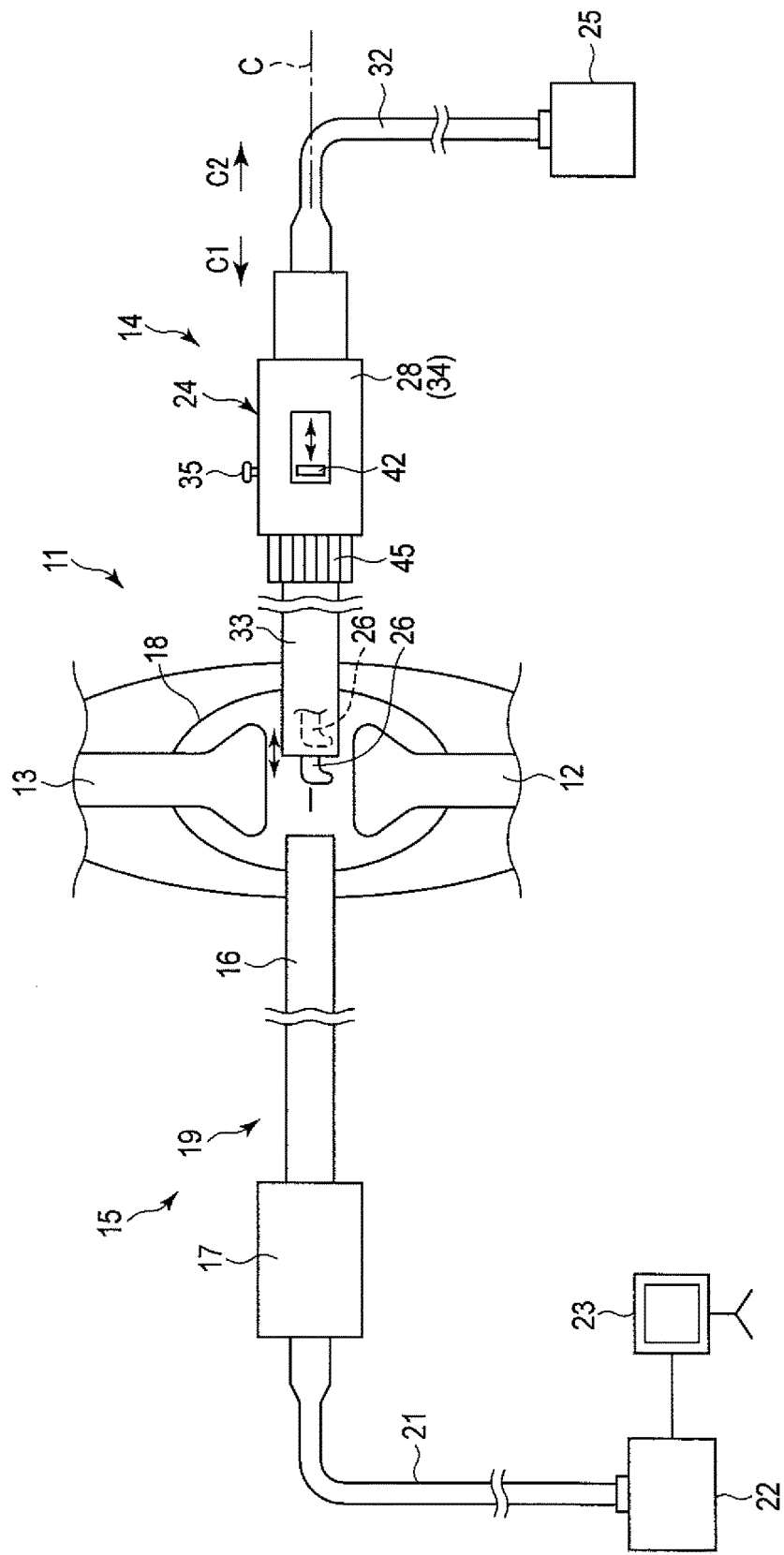
F I G. 1

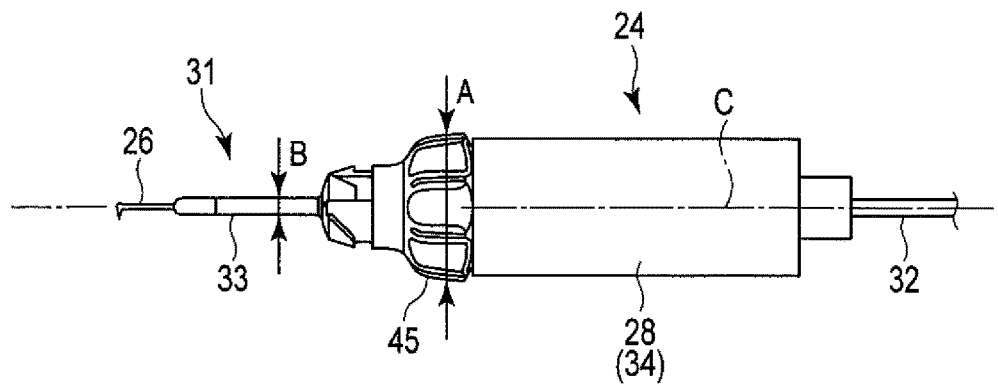
F I G. 2
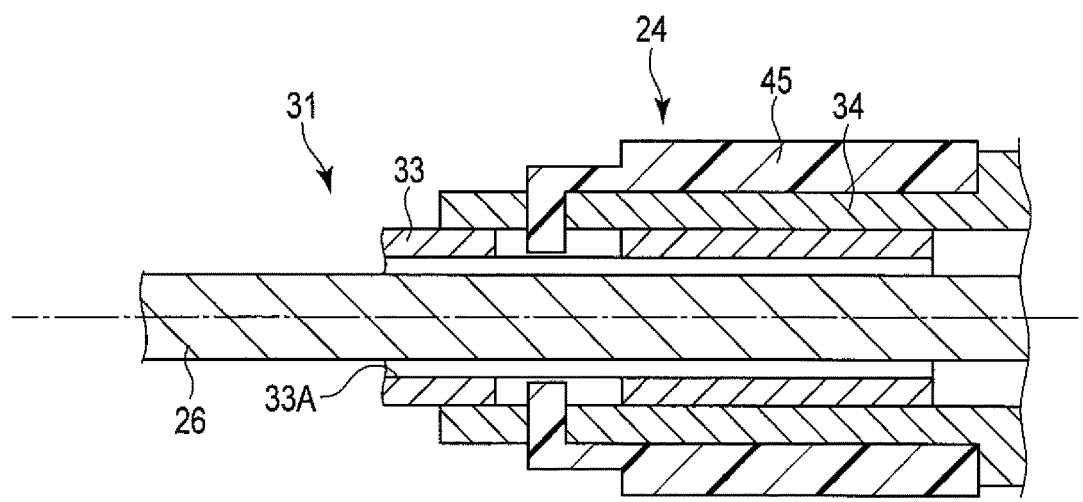
F I G. 3

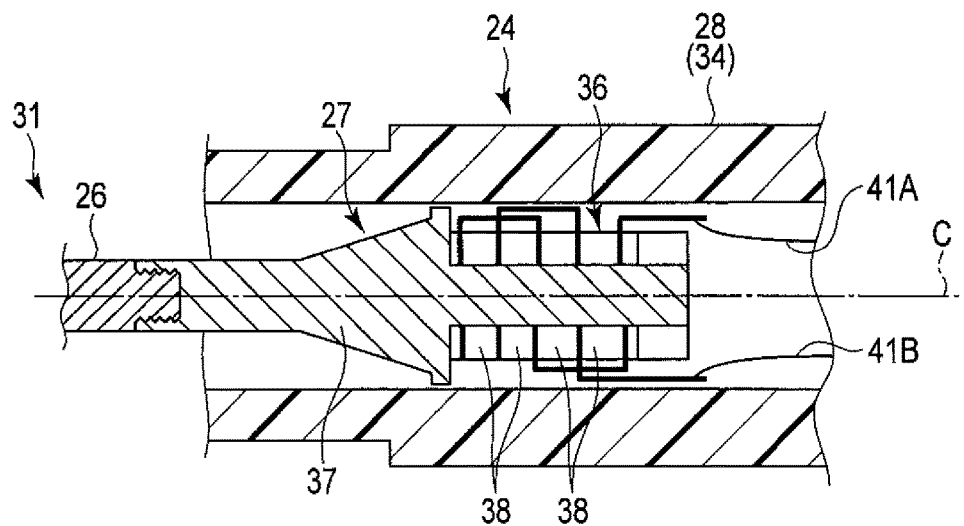
F I G. 4
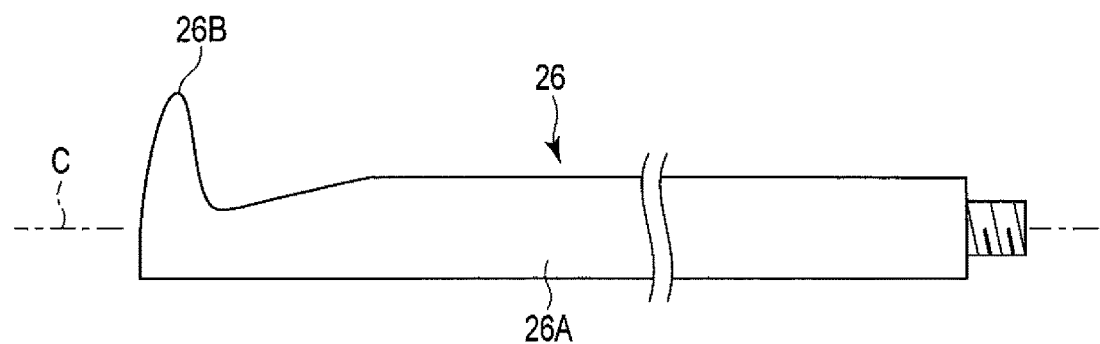
F I G. 5

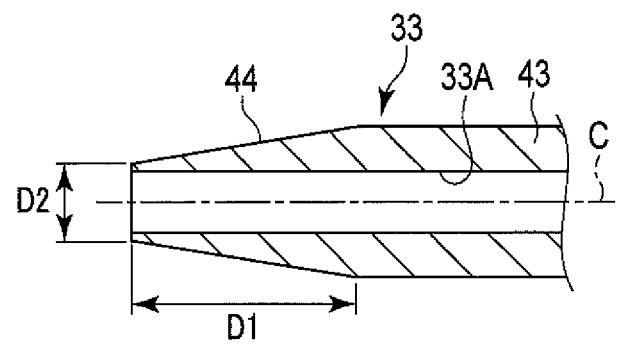
F I G. 11
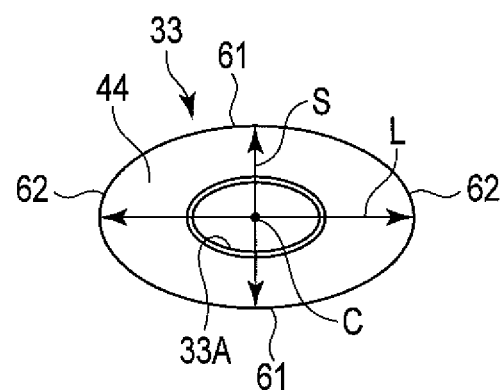
F I G. 12
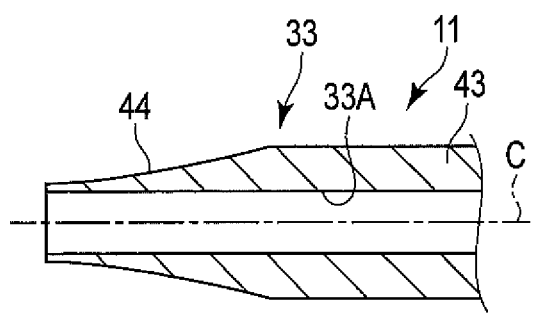
F I G. 13

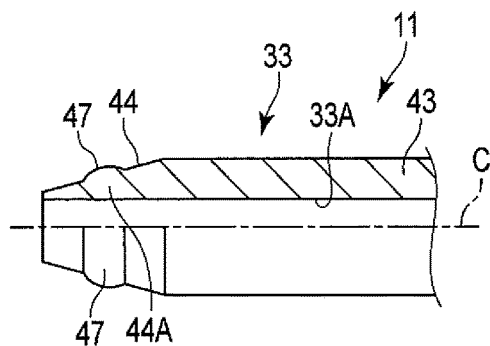
F I G. 17
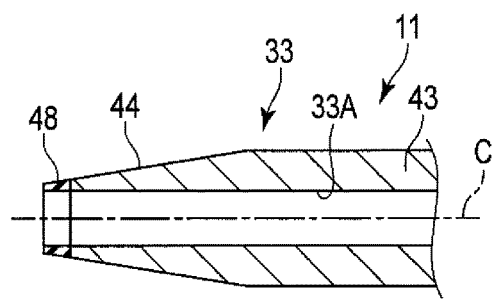
F I G. 18
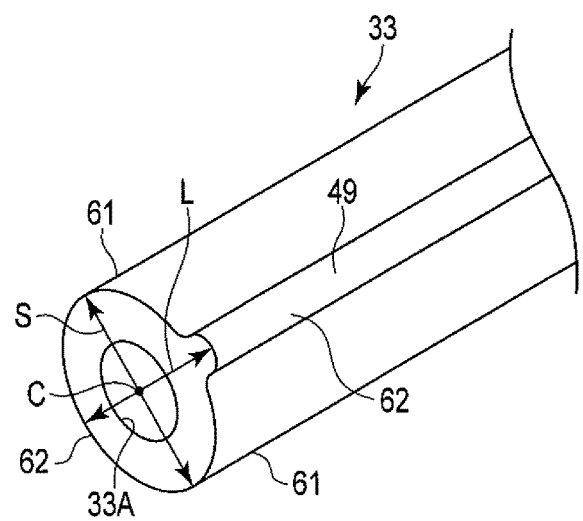
F I G. 19

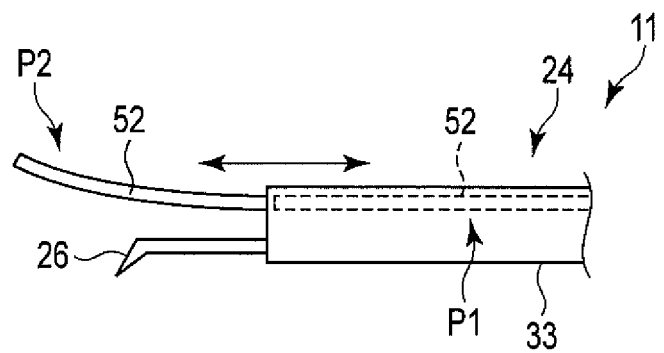
F I G. 22
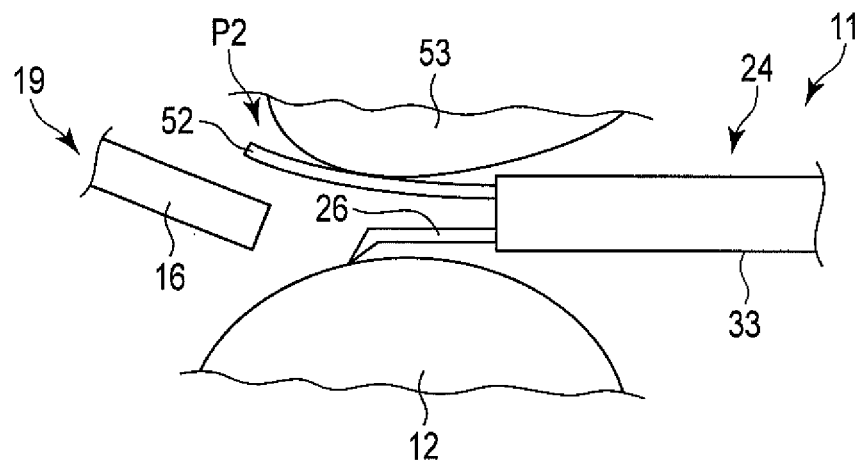
F I G. 23

PROBE UNIT, TREATMENT INSTRUMENT, AND TREATMENT SYSTEM

CROSS-REFERENCE TO RELATED APPLICATIONS

This application is a Continuation Application of PCT Application No. PCT/JP2014/054466, filed Feb. 25, 2014; the PCT Application No. PCT/JP2014/054466 is claiming the benefit of U.S. Provisional Patent Application No. 61/883,520, filed Sep. 27, 2013; the entire contents of which are incorporated herein by reference.

BACKGROUND OF THE INVENTION

1. Field of the Invention

The present invention relates to a probe unit for a treatment using ultrasonic vibration. The present invention also relates to a treatment instrument comprising the probe unit, and a treatment system comprising the treatment instrument.

2. Description of the Related Art

Heretofore, there has been known an ultrasonic surgical instrument for treating a hard tissue such as bone by ultrasonic vibration. For example, an ultrasonic surgical handpiece disclosed in Jpn. Pat. Appln. KOKAI Publication No. 2008-119250 comprises a horn which transmits ultrasonic vibration, and an outer cylindrical portion which covers the horn except for its distal end. This ultrasonic surgical handpiece vibrates the horn in its axial direction at a predetermined frequency, and cuts a predetermined part with the distal end which abuts on a hard tissue such as a bone.

BRIEF SUMMARY OF THE INVENTION

A probe unit includes, a probe configured to treat a bone by ultrasonic vibration, a hollow sheath which surrounds the probe and which has a first portion at a small distance from a central axis, and a second portion at a greater distance from the central axis than the first portion; and a knob configured to rotate the sheath relative to the probe between a first position for insertion between the bone and a living tissue facing the bone so that the first portion is located between the bone and the living tissue and a second position for insertion between the bone and the living tissue so that the second portion is located between the bone and the living tissue.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing a treatment system according to a first embodiment of the present invention;

FIG. 2 is a side view showing a treatment instrument of the treatment system shown in FIG. 1;

FIG. 3 is a sectional view showing the treatment system shown in FIG. 2 cut in a plane which extends along the longitudinal axis of a probe;

FIG. 4 is a sectional view showing a peripheral structure of a vibrator unit included in the treatment system shown in FIG. 2;

FIG. 5 is a side view showing the probe of the treatment instrument shown in FIG. 2;

FIG. 11 is a sectional view showing a part surrounding a tapered portion of the sheath according to a first modification of the first embodiment;

FIG. 12 is a front view showing the part surrounding the tapered portion of the sheath according to the first modification of the first embodiment;

FIG. 13 is a sectional view showing the part surrounding the tapered portion of the sheath according to a second modification of the first embodiment;

FIG. 17 is a partially broken side view showing the part surrounding the tapered portion of the sheath according to a sixth modification of the first embodiment;

FIG. 18 is a sectional view showing the part surrounding the tapered portion of the sheath according to a seventh modification of the first embodiment;

FIG. 19 is a perspective view showing a part located in the vicinity of the sheath according to an eighth modification of the first embodiment;

FIG. 22 is a schematic diagram showing the configuration of a probe unit in the treatment system according to a third embodiment; and FIG. 23 is a schematic diagram showing a condition in which a dilator is moved to the second position in the treatment system according to the third embodiment.

DESCRIPTION OF EMBODIMENTS

First Embodiment

Figure 6:
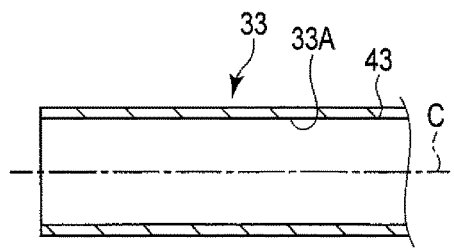
FIG. 6 is a sectional view showing a part surrounding the distal end of a sheath of the treatment instrument shown in FIG. 2.

A first embodiment of the present invention will be described with reference to FIG. 1 to FIG. 10. As shown in FIG. 1, a treatment system 11 is used in a treatment of a joint between a first bone 12 and a second bone 13, for example, in a shoulder, a knee, or an elbow. The treatment system 11 comprises an ultrasonic treatment device 14, an endoscopic device 15, and an arthroscope 19.

The endoscopic device 15 comprises the arthroscope 19, an image processing unit 22, and a display unit 23.

The arthroscope 19 comprises an insertion portion 16 and a holding portion 17. In a treatment that uses the treatment system 11, the distal end of the insertion portion 16 is inserted into an articular cavity 18. One end of a universal cord 21 is connected to the holding portion 17. The other end of the universal cord 21 is connected to the image processing unit 22, for example, an image processor. The image processing unit 22 is electrically connected to the display unit 23, for example, a monitor.

An image pickup device is provided at the distal end of the insertion portion 16. The image pickup device images a subject through an observation window. The image pickup device is electrically connected to the image processing unit 22 via an imaging cable extending through the insertion portion 16, the holding portion 17, and the universal cord 21. An imaged subject figure is subjected to image processing by the image processing unit 22. The subject figure which has been subjected to the image processing is displayed on the display unit 23. An unshown light source unit is connected to the arthroscope 19, and light emitted from the arthroscope 19 is applied to the subject.

The ultrasonic treatment device 14 comprises a treatment instrument 24 (handpiece) and a power supply unit 25. The treatment instrument 24 has a longitudinal axis C. Here, one of two directions parallel to the longitudinal axis C is a distal direction (direction of an arrow C1 in FIG. 1), and the direction opposite to the distal direction is a proximal direction (direction of an arrow C2 in FIG. 1). The longitudinal axis C corresponds to the longitudinal axis of a later-described probe 26.

As shown in FIG. 2 and FIG. 4, the treatment instrument 24 comprises a vibrator unit 27, a grip portion 28, and a probe unit 31. One end of a cable 32 is connected to the grip portion 28. The other end of the cable 32 is connected to the power supply unit 25. The probe unit 31 has a sheath 33 and the probe 26.

The grip portion 28 comprises a cylindrical holding case 34 extending along the longitudinal axis C. A doctor who is a user can use the treatment instrument 24 by gripping the holding case 34. The vibrator unit 27 is inserted into the holding case 34 from the side of the proximal direction, and the sheath 33 is inserted into the holding case 34 from the side of the distal direction. The probe 26 is inserted through the sheath 33. The probe 26 is coupled to the vibrator unit 27 inside the holding case 34. As shown in FIG. 1, an energy operation input button 35 is attached to the holding case 34. The probe 26 protrudes toward the distal direction from the distal end of the sheath 33.

As shown in FIG. 4, the vibrator unit 27 comprises an ultrasonic vibrator 36 and a horn member 37. Piezoelectric elements 38 (four piezoelectric elements in the present embodiment) which change an electric current into ultrasonic vibration are provided in the ultrasonic vibrator 36. One end of each of electric wiring lines 41A and 41B is connected to the ultrasonic vibrator 36. Each of the electric wiring lines 41A and 41B extends through the cable 32, and has the other end connected to the power supply unit 25. Ultrasonic vibration is generated in the ultrasonic vibrator 36 by the supply of electric power from the power supply unit 25 to the ultrasonic vibrator 36 via the electric wiring lines 41A and 41B.

The horn member 37 is attached to the ultrasonic vibrator 36. The ultrasonic vibration generated in the ultrasonic vibrator 36 is transmitted to the horn member 37. The horn member 37 is made of a metallic material. The horn member 37 is provided with a sectional area changing portion in which the sectional area perpendicular to the longitudinal axis C deceases in the distal direction. The amplitude of the ultrasonic vibration is increased by the sectional area changing portion. The distal end of the horn member 37 is connected to the proximal end of the probe 26 by, for example, a screw structure. The probe 26 is coupled to the vibrator unit 27 by this structure. The vibrator unit 27 and the probe 26 can slide in the direction of the longitudinal axis C by the sliding of a finger hook portion 42 shown in FIG. 1 in the direction of the longitudinal axis C. A treatment portion 26B of the probe 26 can be housed in the sheath 33 or protruded from the distal end of the sheath 33 by the operation of the finger hook portion 42. A buffer material (elastic material) for absorbing vibration generated from the vibrator unit 27 may be provided between the inner circumferential surface of the holding case 34 and the vibrator unit 27.

The probe 26 is made of, for example, a metallic material. As shown in FIG. 5, the probe 26 comprises a probe body 26A extending along the longitudinal axis C, and the treatment portion 26B provided on the proximal direction side of the probe body 26A. The ultrasonic vibration generated in the ultrasonic vibrator 36 is transmitted to the probe body 26A of the probe 26 via the horn member 37. In the probe body 26A, the ultrasonic vibration is transmitted from the proximal direction to the distal direction. The treatment portion 26B treats a treatment target (bone or living tissue) by using the ultrasonic vibration transmitted via the probe body 26A. In the present embodiment, the probe 26 makes vertical vibration in which the vibration direction is parallel to the distal direction and the proximal direction while ultrasonic vibration is being transmitted. The treatment portion 26B is provided at the distal end of the probe body 26A, and has, for example, a hook shape or a rake shape.

Figure 7:
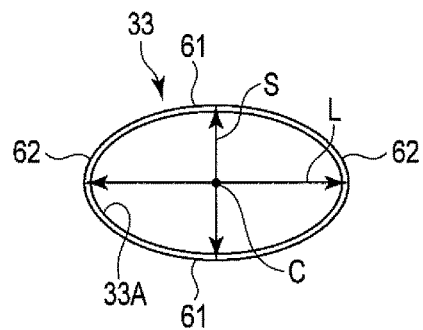
FIG. 7 is a front view of the sheath shown in FIG. 6 from a front direction.

As shown in FIG. 3, FIG. 6, and FIG. 7, the sheath 33 has a distal end and a proximal end, has a hollow and elliptical sectional shape, and surrounds the probe 26. The sheath 33 is made of, for example, a metallic material. The sheath 33 has an insertion hole 33A, and the probe 26 can be put through the insertion hole 33A.

As shown in FIG. 2, FIG. 3, and FIG. 6, the sheath 33 has an elliptic tubular body portion 43. Although the sheath 33 according to the present embodiment has an elliptic sectional shape over the entire length from the distal end to the proximal end, at least part of the distal side may have an elliptic sectional shape. A knob 45 which is provided integrally with the body portion 43 is provided on the proximal side of the body portion 43. As shown in FIG. 7, the sheath 33 has a long diameter L, and a short diameter S that intersects (at right angles) with the long diameter L. In the present embodiment, the distance from the central axis C (longitudinal axis C) of the sheath 33 to the outer circumferential surface of the sheath 33 may vary according to the position of the outer circumferential surface. In a first portion 61 which is a portion corresponding to the short diameter S and its vicinity, the distance from the center (longitudinal axis C) of the sheath 33 to the outer circumferential surface of the sheath 33 is the shortest. In contrast, in a second portion 62 which is a portion corresponding to the long diameter L and its vicinity, the distance from the central axis C (longitudinal axis C) of the sheath 33 to the outer circumferential surface of the sheath 33 is the longest. As shown in FIG. 2, a diameter A of the knob 45 has a size which is several times to 20 times a diameter B of the body portion 43 of the sheath 33. The doctor can rotate the sheath 33 around the longitudinal axis C with little force by putting fingers on the knob 45 and rotating the knob 45.

Figure 8:
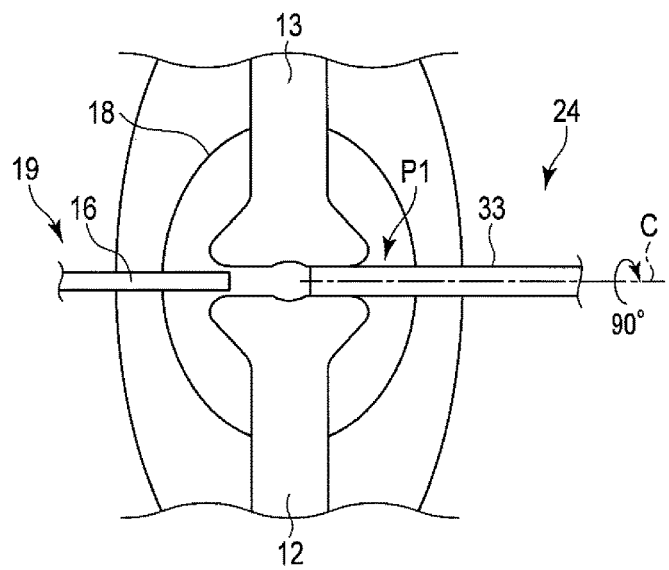
FIG. 8 is a schematic diagram showing a condition in which the sheath is located at a first position in the treatment system according to the first embodiment.
Figure 9:
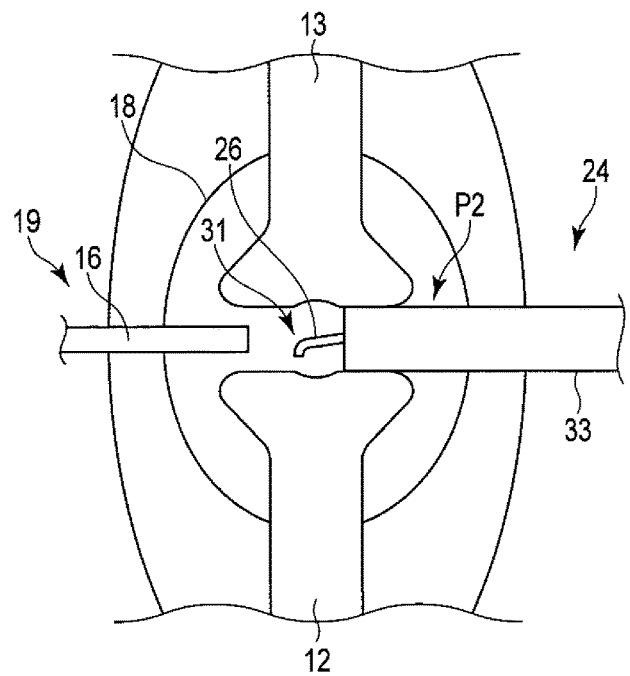
FIG. 9 is a schematic diagram showing a condition in which the sheath is located at a second position in the treatment system according to the first embodiment.
Figure 10:
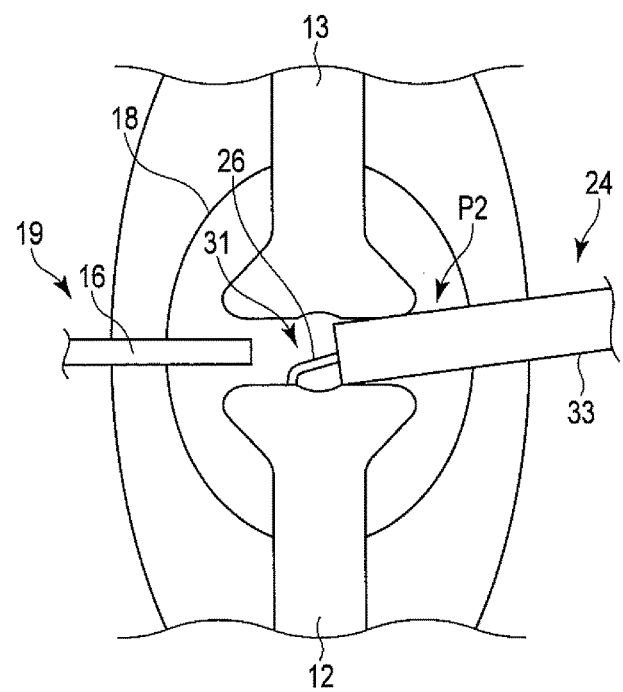
FIG. 10 is a schematic diagram showing a condition in which, for example, the angle of the sheath is adjusted to treat a bone with the probe in the treatment system according to the first embodiment.

The functions of the treatment system 11 according to the present embodiment (an arthroscopic surgical method that uses the treatment system 11) are described with reference to FIG. 8 to FIG. 10. As shown in FIG. 8, the doctor inserts the insertion portion 16 of the arthroscope 19 into the articular cavity 18. While observing with the arthroscope 19, the doctor inserts the sheath 33 of the ultrasonic treatment device 14 into the articular cavity 18. In this instance, the probe 26 can be used to remove part of an articular capsule around the articular cavity 18. Thus, the same probe 26 for the treatment of the later-described first bone 12 can be used, and there is no need to replace the treatment instrument 24.

The sheath 33 is inserted between the first bone 12 and the second bone 13 which is an example of a living tissue facing the first bone 12. In this instance, the sheath 33 is adjusted by the knob 45 so that the first portion 61 is located between the first bone 12 and the second bone 13 as shown in FIG. 7 and FIG. 8. While the first portion 61 is being located between the first bone 12 and the second bone 13, the sheath 33 is inserted between the first bone 12 and the second bone 13 (this is referred to as a first position P1). In other words, the sheath 33 is inserted between the first bone 12 and the second bone 13 so that the long diameter L of the sheath 33 is horizontal (a direction that intersects at right angles with a direction in which the first bone 12 and the second bone 13 are connected) as shown in FIG. 7.

The first portion 61 of the sheath 33 is thus located between the first bone 12 and the second bone 13 by the operation of the knob 45, so that the sheath 33 can be more easily inserted between the first bone 12 and the second bone 13. At this stage, the treatment portion 26B of the probe 26 is housed in the sheath 33 by the finger hook portion 42.

The doctor then rotates the knob 45, for example, 90° clockwise or counterclockwise relative to the grip portion 28 with his/her hand or finger. Thus, the sheath 33 rotates, for example, 90° clockwise or counterclockwise at the position between the first bone 12 and the second bone 13. As a result, as shown in FIG. 9, the second portion 62 of the sheath 33 is located between the first bone 12 and the second bone 13 (the long diameter L is located between the first bone 12 and the second bone 13), and the gap between the first bone 12 and the second bone 13 is increased (this is referred to as a second position P2).

That is, the sheath 33 according to the present embodiment has a shape in which the distance from the center of the sheath 33 to the outer circumferential surface has the long diameter L that is a first diameter and the short diameter S that is a second diameter smaller than the first diameter; for example, the sheath 33 has an elliptic sectional shape. Therefore, if the sheath 33 which is being located between the first bone 12 and the second bone 13 is rotated around the central axis C by the operation of the knob 45, the gap between the first bone 12 and the second bone 13 can be increased. Thus, it is possible to ensure sufficient space for the treatment portion 26B of the probe 26 to treat the living tissue. In this state, the finger hook portion 42 is operated to protrude the probe 26 from the sheath 33. The angle of the sheath 33 and the position and angle of the probe 26 are finely adjusted to conduct a treatment of, for example, shaving a treatment target bone as shown in FIG. 10. This treatment includes various treatments such as removal of a bone spur and other living tissues. A regulation member is provided which regulates the rotation of the knob 45 so that the sheath 33 does not rotate around the longitudinal axis at the first position P1 or the second position P2. In other words, a regulation member may be provided to regulate the rotation of the knob 45 to prevent the sheath 33 from rotating around the longitudinal axis when the gap between the first bone 12 and the second bone 13 is at the first position P1, and to regulate the rotation of the knob 45 to prevent the sheath 33 from rotating around the longitudinal axis when the gap between the first bone 12 and the second bone 13 is at the second position P2 where the gap is larger than at the first position P1.

According to the first embodiment, the probe unit 31 comprises the probe 26, the sheath 33, and the knob 45. The probe 26 can treat the bone by ultrasonic vibration. The hollow sheath 33 surrounds the probe 26. The sheath 33 has the first portion 61 at a small distance from the central axis C, and the second portion 62 at a greater distance from the central axis C than the first portion 61. The knob 45 can rotate the sheath 33 relative to the probe 26 between the first position P1, which is inserted between the first bone 12 and the living tissue so that the second portion 62 is located between the first bone 12 and the living tissue facing the first bone 12, and the second position P2 which is inserted between the first bone 12 and the living tissue so that the first portion 61 is located between the first bone 12 and the living tissue.

According to this configuration, even when the gap between the first bone 12 and the living tissue is small, the sheath 33 can be inserted so that the short diameter S of the elliptic sheath 33 is located in this gap. In particular, a treatment instrument which is an ultrasonically vibrating type as in the present embodiment can be formed thinner than a conventional motor-driven rotary treatment instrument (a type of treatment instrument provided with a large number of cutting tools on the circumference of a treatment shaft), and can therefore easily reach even a small gap. Moreover, in the case of the ultrasonically vibrating type treatment instrument, there is a lower risk that surrounding living tissues may be damaged by the rebounding of the cutting tools as in the rotary treatment instrument.

Furthermore, according to the configuration described above, it is possible to widen the gap without using an additional instrument by rotating the sheath 33 from the first position P1 to the second position P2. While the gap is being thus widened, the first bone 12 and the living tissue can be treated. This can considerably improve convenience for the doctor at the time of a surgical operation. Moreover, it is possible to obtain a mechanism which can adjust the gap between the first bone 12 and the living tissue by a simple configuration as above, simplify the configurations of the probe unit 31 and the treatment system 11, and reduce the number of instruments necessary for an operation. Furthermore, there is no need for an instrument to widen the gap between the first bone 12 and the living tissue, so that it is not necessary to cut, for example, the skin of a patient to put through the instrument, and stress on the patient can be reduced. The sheath 33 can rotate relative to the sheath 33, so that after the rotation of the sheath 33, the probe 26 can be rotated relative to the sheath 33 to finely adjust the position of the probe 26.

The sheath 33 is elliptic. Thus, a simple form of the structure of the sheath 33 having the first portion 61 and the first portion 61 can be obtained.

The sheath 33 comprises the elliptic body portion 43, and the knob 45, which has a diameter larger than that of the body portion 43, and on which the hand can be put to rotate the sheath 33. According to this configuration, it is possible to reduce the force necessary to rotate the sheath 33, and reduce a burden on the doctor at the time of an operation.

Although the sheath 33 is elliptic in the present embodiment described, it is also preferable that the sheath 33 has a substantially elliptic cross section in which a flat surface and semicircles are continuous, for example, as in an athletic track. Although briefly described below, the elliptic shape also includes the substantially elliptic shape in which the flat surface and semicircles are continuous. Although the finger hook portion 42 is provided in the example described in the present embodiment, no finger hook portion 42 may be provided in the treatment instrument 24, and the position of the probe 26 may be fixed. In this example, the size of the treatment portion 26B of the probe 26 is smaller than the diameters of the sheath 33 (the long diameter L and the short diameter S of the elliptic distal end). Thus, the treatment portion 26B of the probe 26 does not block the operation when the sheath 33 is inserted between the first bone 12 and the second bone 13 (the living tissue). That is, in the present embodiment, the finger hook portion 42 is not an essential component in the treatment instrument 24.

Next, a first modification of the treatment system 11 in which the shape of the sheath 33 is partly modified is described with reference to FIG. 11 and FIG. 12. In the present modification, the shape of the sheath 33 is partly different, but other parts are the same as those in the first embodiment. The sheath 33 has a hollow and elliptic sectional shape.

The sheath 33 has a tapered portion 44, and the tapered portion 44 is provided on the distal side of the body portion 43. As shown in FIG. 11 and FIG. 12, the tapered portion 44 becomes smaller in diameter as the distance to the distal end of the sheath 33 decreases. The tapered portion 44 has what is known as a truncated cone shape. A length D1 of the tapered portion 44 in the direction of the longitudinal axis C of the probe 26 is greater than a diameter D2 of the distal end of the tapered portion 44 (the long diameter L and the short diameter S of the elliptic distal end).

According to the present modification, even when the gap between the first bone 12 and the living tissue is smaller, it is possible to more easily insert the sheath 33 into this gap. The length of the tapered portion 44 along the direction of the longitudinal axis C of the probe 26 is greater than the diameter of the distal end of the tapered portion 44. According to this configuration, the inclination of the tapered portion 44 relative to the longitudinal axis C of the probe 26 can be gentler. Thus, it is possible to reduce the risk that the sheath 33 may damage the first bone 12 and the living tissue when the sheath 33 is inserted into the gap between the first bone 12 and the living tissue.

Next, a second modification of the treatment system 11 in which the shape of the sheath 33 is partly modified is described with reference to FIG. 13. In the present modification, part of the shape of the sheath 33 is different, but other parts are the same as those in the first embodiment. The sheath 33 has a hollow and elliptic sectional shape.

In the present modification, the tapered portion 44 does not have a simple truncated cone shape, but is curved so that the surface of the tapered portion 44 becomes parallel to the longitudinal axis C of the probe 26 as the distance to the distal end of the sheath 33 decreases. Thus, it is possible to reduce the resistance applied to the sheath 33 when the sheath 33 is inserted into the gap between the first bone 12 and the living tissue. Thus, it is possible to further reduce the risk that the first bone 12 and the living tissue may be damaged when the sheath 33 is inserted as in the first embodiment.

Figure 14:
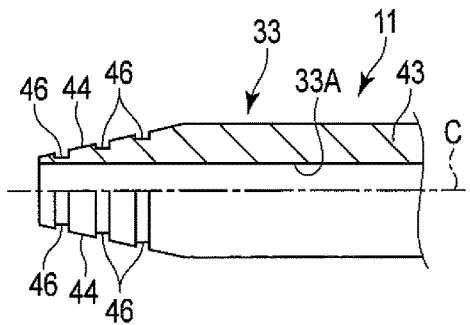
FIG. 14 is a partially broken side view showing the part surrounding the tapered portion of the sheath according to a third modification of the first embodiment.

Furthermore, a third modification of the treatment system 11 in which the shape of the sheath 33 is partly modified is described with reference to FIG. 14. In the present modification, the shape of the sheath 33 is partly different, but other parts are the same as those in the first embodiment. The sheath 33 has a hollow and elliptic sectional shape.

In the present modification, grooves 46 are provided in the tapered portion 44. The grooves 46 are ring-shaped in the tapered portion 44. As shown in FIG. 14, the grooves 46 extend in a direction that intersects with the longitudinal axis C of the probe 26. Thus, after the sheath 33 is inserted into the gap between the first bone 12 and the living tissue to rotate the sheath from the first position P1 to the second position P2, the tapered portion 44 located around the grooves 46 can be engaged (caught) with the first bone 12 and the living tissue. In this way, it is possible to prevent the tapered portion 44 of the sheath 33 from coming off the gap when the first bone 12 is treated. It is also preferable that the grooves 46 are not ring-shaped but helical.

Figure 15:
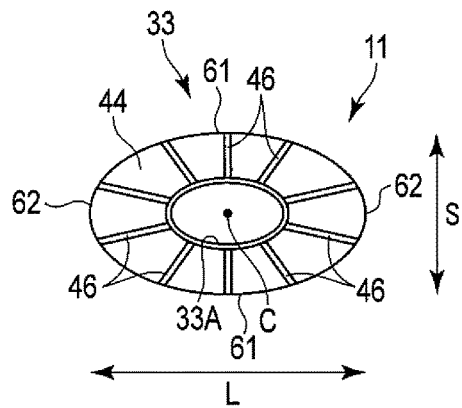
FIG. 15 is a front view showing the tapered portion of the sheath according to a fourth modification of the first embodiment from a front direction.

Furthermore, a fourth modification of the treatment system 11 in which the shape of the sheath 33 is partly modified is described with reference to FIG. 15. In the present modification, the shape of the sheath 33 is partly different, but other parts are the same as those in the first embodiment. The sheath 33 has a hollow and elliptic sectional shape.

In the present modification, grooves 46 are provided in the tapered portion 44. As shown in FIG. 15, the grooves 46 are radially formed on the tapered portion 44 around the longitudinal axis C of the probe 26. The grooves 46 are provided to depress from the circumference of the tapered portion 44. Thus, after the sheath 33 is inserted into the gap between the first bone 12 and the living tissue to rotate the sheath 33 from the first position P1 to the second position P2, the tapered portion 44 located around the grooves 46 can be engaged (caught) with the first bone 12 and the living tissue. In this way, it is possible to prevent the tapered portion 44 of the sheath 33 from coming off the gap when the first bone 12 is treated. According to the present modification, the grooves 46 are provided in a direction along the direction in which the sheath 33 is pulled and inserted, so that it is possible to reduce the risk that the first bone 12 and the living tissue may be damaged when the sheath 33 is pulled and inserted.

Figure 16:
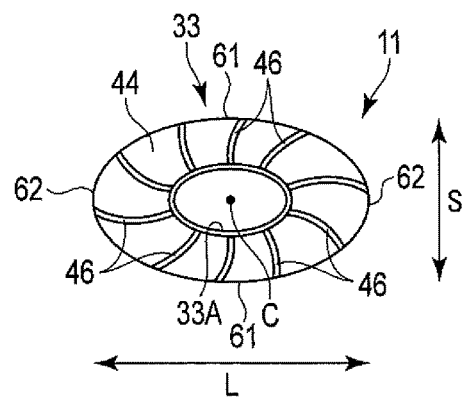
FIG. 16 is a front view showing the tapered portion of the sheath according to a fifth modification of the first embodiment from a front direction.

A fifth modification of the treatment system 11 in which the shape of the sheath 33 is partly modified is described with reference to FIG. 16. In the present modification, part of the shape of the sheath 33 is different, but other parts are the same as those in the first embodiment. The sheath 33 has a hollow and elliptic sectional shape.

In the present modification, grooves 46 are provided in the tapered portion 44. As shown in FIG. 16, the grooves 46 are helically provided on the tapered portion 44 around the longitudinal axis C of the probe 26. The grooves 46 are provided to depress from the circumference of the tapered portion 44. Thus, after the sheath 33 is inserted into the gap between the first bone 12 and the living tissue to rotate the sheath 33 from the first position P1 to the second position P2, the tapered portion 44 located around the grooves 46 can be engaged (caught) with the first bone 12 and the living tissue. In this way, it is possible to prevent the tapered portion 44 of the sheath 33 from coming off the gap when the first bone 12 is treated.

A sixth modification of the treatment system 11 in which part of the shape of the sheath 33 is modified is described with reference to FIG. 17. In the present modification, part of the shape of the sheath 33 is different, but other parts are the same as those in the first embodiment. The sheath 33 has a hollow and elliptic sectional shape.

In the present modification, one or more circular-ring-shaped bulges 47 are provided on the tapered portion 44. As shown in FIG. 17, the bulge 47 bulges from a body portion 44A of the tapered portion 44 in a direction away from the longitudinal axis C of the probe 26. The bulge 47 has a semicircular sectional shape. According to the sheath 33 in this modification, after the sheath 33 is inserted into the gap between the first bone 12 and the living tissue to rotate the sheath 33 from the first position P1 to the second position P2, the bulge 47 can be engaged (caught) with the first bone 12 and the living tissue. In this way, it is possible to prevent the tapered portion 44 of the sheath 33 from coming off the gap when the first bone 12 is treated.

A seventh modification of the treatment system 11 in which part of the shape of the sheath 33 is modified is described with reference to FIG. 18. In the present modification, part of the shape of the sheath 33 is different, but other parts are the same as those in the first embodiment. The sheath 33 has a hollow and elliptic sectional shape.

In the present modification, a living tissue protection member 48 is provided at the distal end of the tapered portion 44. As shown in FIG. 18, the living tissue protection member 48 is annular, and covers the distal end of the tapered portion 44 which is also annular. The living tissue protection member 48 is made of, for example, a resinous material. More specifically, the living tissue protection member 48 is made of a resinous material such as polytetrafluoro-ethylene or silicon rubber. According to the sheath 33 in this modification, the living tissue protection member 48 can prevent the distal end of the tapered portion 44 from directly contacting the first bone 12 and the living tissue. Consequently, it is possible to further reduce the risk that the first bone 12 and the living tissue may be damaged by the sheath 33 when the sheath 33 is inserted into the gap between the first bone 12 and the living tissue.

An eighth modification of the treatment system 11 in which the shape of the sheath 33 is partly modified is described with reference to FIG. 19. In the present modification, part of the shape of the sheath 33 is different, but other parts are the same as those in the first embodiment. The sheath 33 has a hollow and substantially circular cylindrical sectional shape.

In the present modification, one or more projections 49 having a substantially semicircular sectional shape are provided on the extension of the sheath 33 (one projection is provided in the case shown in the present modification). As shown in FIG. 19, the projection 49 is provided straight on the sheath 33 along the longitudinal axis C. This projection 49 may be provided over the entire length of the sheath 33, or may be provided a predetermined length from the distal side of the sheath 33 toward the proximal side.

The sheath 33 has a long diameter L, and a short diameter S that intersects (at right angles) with the long diameter L. That is, in the present modification, the distance from the center (longitudinal axis C) of the sheath 33 to the outer circumferential surface of the sheath 33 varies according to the position of the outer circumferential surface. In a first portion 61 which is a portion corresponding to the short diameter S and its vicinity, the distance from the central axis C (longitudinal axis C) of the sheath 33 to the outer circumferential surface of the sheath 33 is the shortest. In contrast, in a second portion 62 which is a portion corresponding to the long diameter L and its vicinity, the distance from the central axis C (longitudinal axis C) of the sheath 33 to the outer circumferential surface of the sheath 33 is the longest.

In the present modification, the doctor inserts the sheath 33 between the first bone 12 and the second bone 13 so that the first portion 61 (short diameter) is located between the first bone 12 and the second bone 13 (the living tissue) (the first position P1). The doctor then rotates the knob 45, for example, 90° clockwise or counterclockwise relative to the grip portion 28 with his/her hand or finger. Thus, the sheath 33 rotates, for example, 90° clockwise or counterclockwise at the position between the first bone 12 and the second bone 13. As a result, the second portion 62 of the sheath 33 is located between the first bone 12 and the second bone 13 (the long diameter L is located between the first bone 12 and the second bone 13), and the gap between the first bone 12 and the second bone 13 is increased (the second position P2). The angle of the sheath 33 and the position and angle of the probe 26 are then finely adjusted to conduct a treatment of, for example, shaving a treatment target bone.

According to the sheath 33 in this modification, it is possible to widen the gap without using an additional instrument by inserting the sheath 33 into the gap between the first bone 12 and the living tissue, and then rotating the sheath 33 from the first position P1 to the second position P2. While the gap is being thus widened, the first bone 12 and the living tissue can be treated by the probe 26.

Second Embodiment

The treatment system 11 according to a second embodiment is described with reference to FIG. 20 and FIG. 21. The treatment system 11 according to the second embodiment is different from that according to the first embodiment in that an inflation member 51 such as a balloon is attached to the outer circumferential surface of the sheath 33, but is the same as that in the first embodiment in other respects. Therefore, mainly the differences between the first embodiment and the second embodiment are described, and the same parts as those in the first embodiment are neither shown nor described.

The treatment instrument 24 comprises the vibrator unit 27, the grip portion 28, and the probe unit 31. The probe unit 31 has the sheath 33, the probe 26, and the inflation member 51 provided in the vicinity of the end of the sheath 33. The vibrator unit 27, the grip portion 28, and the probe 26 have configurations similar to those in the first embodiment.

The sheath 33 has, for example, a hollow and circular sectional shape, and surrounds the probe 26. The sheath 33 is made of, for example, a metallic material. The sheath 33 may have the tapered portion 44 on the distal side as in the first embodiment. In this case, the tapered portion 44 of the sheath 33 may be modified as in the first to seventh modifications of the first embodiment.

Figure 20:
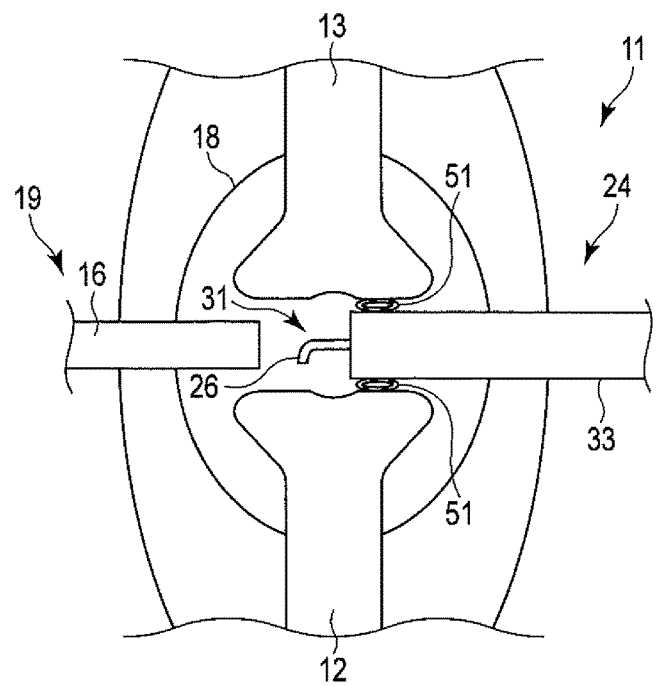
FIG. 20 is a schematic diagram showing a condition before the inflation of an inflation member in the treatment system according to a second embodiment.

As shown in FIG. 20, the inflation member 51 is attached to the outer circumferential surface of the sheath 33 in the vicinity of the distal end of the sheath 33. The inflation member 51 comprises, for example, a circular-ring-shaped balloon, and can be freely inflated or deflated by supplying air from an unshown pump unit.

The functions of the treatment system 11 according to the present embodiment (a surgical method that uses the treatment system 11) are described with reference to FIG. 20 and FIG. 21. As shown in FIG. 20, the doctor inserts the insertion portion 16 of the arthroscope 19 into the articular cavity 18. While observing with the arthroscope 19, the doctor inserts the sheath 33 of the ultrasonic treatment device 14 into the articular cavity 18. In this instance, the probe 26 can be used to remove part of an articular capsule around the articular cavity 18. The sheath 33 is then inserted between the first bone 12 and the second bone 13 which is an example of a living tissue facing the first bone 12. One part of the inflation member 51 intervenes between the sheath 33 and the first bone 12, and the other part of the inflation member 51 intervenes between the sheath 33 and the living tissue (e.g. the second bone 13).

Figure 21:
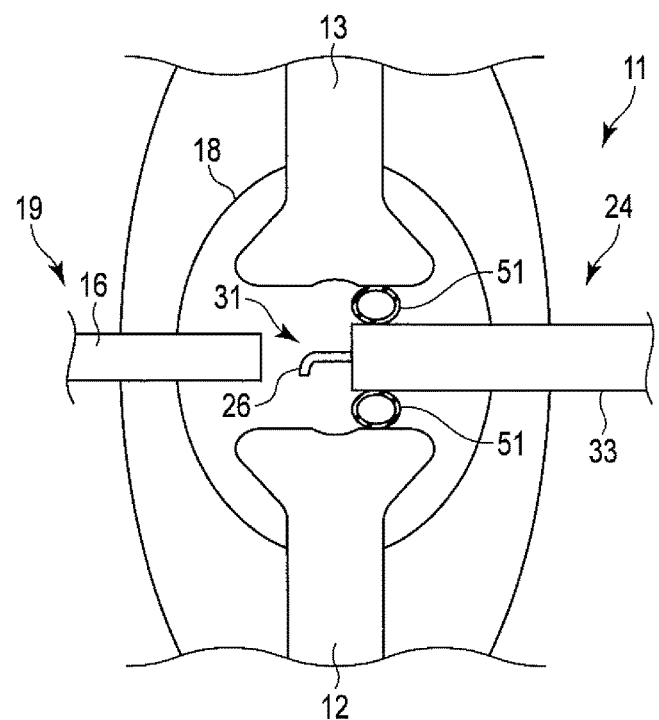
FIG. 21 is a schematic diagram showing a condition after the inflation of the inflation member in the treatment system according to the second embodiment.

The doctor then inflates the inflation member 51 as shown in FIG. 21. In this way, the gap between the first bone 12 and the second bone 13 can be increased. In this state, the angle of the sheath 33 and the position and angle of the probe 26 are then finely adjusted to conduct a treatment of, for example, shaving the first bone 12 and the living tissue which are treatment targets.

According to the second embodiment, the probe 26, the sheath 33, and the inflation member 51 are provided. The probe 26 treats the bone by ultrasonic vibration. The hollow sheath 33 surrounds the probe 26. The inflation member 51 intervenes between the sheath 33 and the first bone 12, and can inflate to widen the gap between the first bone 12 and the living tissue (e.g. the second bone 13) facing the first bone 12.

According to this configuration, it is possible to widen the gap between the first bone 12 and the living tissue (e.g. the second bone 13) by the inflation member 51 without using an additional instrument. While the gap is being thus widened, the first bone 12 and the living tissue (e.g. the second bone 13) can be treated. This can considerably improve convenience for the doctor at the time of a surgical operation. Also, there is no need for an additional instrument to widen the gap between the first bone 12 and the living tissue (e.g. the second bone 13), so that it is not necessary to cut, for example, the skin of a patient to put the instrument through, and stress on the patient can be reduced.

In the present embodiment, the inflation member 51 comprises, for example, an annular balloon provided in the outer circumferential portion of the distal end of the sheath 33. Thus, the contact area between the bone as well as the living tissue and the sheath 33 can be increased via the balloon. Thus, an accurate dimension between the first bone 12 and the living tissue can be easily obtained, and accurate positioning between the first bone 12 and the living tissue is possible. This can improve convenience for the doctor at the time of surgery. Further, there is no need for an additional instrument to widen the gap between the first bone 12 and the living tissue, so that it is not necessary to cut, for example, the skin of a patient to put through the instrument, and injury to the patient can be reduced.

Although the sheath 33 described in the present embodiment has a circular cross sectional shape, it is also preferable that the sheath 33 has an elliptic cross sectional shape as has been described in the first embodiment. That is, it is also preferable to use the sheath 33 described in the first embodiment for the sheath 33 in the present embodiment.

Third Embodiment

The treatment system 11 according to a third embodiment is described with reference to FIG. 22 and FIG. 23. The treatment system 11 according to the third embodiment is different from that according to the first embodiment in that a dilator 52 is provided, but is the same as that in the first embodiment in other respects. Therefore, mainly the differences between the first embodiment and the third embodiment are described, and the same parts as those in the first embodiment are neither shown nor described.

The treatment instrument 24 comprises the vibrator unit 27, the grip portion 28, and the probe unit 31. The probe unit 31 has the sheath 33, the probe 26, and the dilator 52 which can be housed in the sheath 33 or protruded from the distal end of the sheath 33. The vibrator unit 27, the grip portion 28, and the probe 26 have configurations similar to those in the first embodiment.

The sheath 33 has, for example, a hollow and circular sectional shape, and surrounds the probe 26. The sheath 33 is made of, for example, a metallic material. The sheath 33 may have the tapered portion 44 on the distal side as in the first embodiment. In this case, the tapered portion 44 of the sheath 33 may be modified as in the first to seventh modifications of the first embodiment.

The dilator 52 comprises a linear member which is provided with a tendency to curve in, for example, one of the radial directions of the sheath 33. More specifically, the dilator 52 is linear as a whole, and comprises a thin plate-shaped member which is warped in one of the radial directions of the sheath 33. The dilator 52 is made of, for example, a metallic material. The dilator 52 can move between the first position P1 to be housed in the sheath 33 and the second position P2 to protrude from the sheath 33. The dilator 52 can be moved between the first position P1 and the second position P2, for example, by sliding an operational lever provided in the holding case 34 in the longitudinal axis direction of the probe 26.

When located at the second position P2, the dilator 52 can widen the gap between the first bone 12 and a synovium 53 which is an example of a living tissue facing the first bone 12.

The functions of the treatment system 11 according to the present embodiment are described with reference to FIG. 22 and FIG. 23. As shown in FIG. 23, the doctor inserts the insertion portion 16 of the arthroscope 19 into the articular cavity 18. While observing with the arthroscope 19, the doctor inserts the sheath 33 of the ultrasonic treatment device 14 into the articular cavity 18 as shown in FIG. 23. In this instance, the probe 26 can be used to remove part of an articular capsule around the articular cavity 18. The sheath 33 is then inserted into, for example, the vicinities of the first bone 12 and the synovium 53 facing the bone.

The doctor then operates the operational lever to protrude the dilator 52 from the distal end of the sheath 33 as shown in FIG. 23. The synovium 53 is moved in a direction away from the first bone 12 by the dilator which is provided with a tendency to curve in one direction. In this way, the gap between the first bone 12 and the synovium 53 can be increased. In this state, the insertion portion 16 of the arthroscope 19 is inserted into the articular cavity 18. In this state, the angle of the sheath 33 and the position and angle of the probe 26 are then adjusted to conduct a treatment of, for example, shaving the treatment target first bone 12.

According to the present embodiment, the probe 26, the sheath 33, and the linear dilator 52 are provided. The probe 26 treats the first bone 12 by ultrasonic vibration. The hollow sheath 33 surrounds the probe 26. The dilator 52 can move between the first position P1 to be housed in the sheath 33 and the second position P2 to protrude from the sheath 33 to widen the gap between the first bone 12 and the living tissue facing the first bone 12.

According to this configuration, it is possible to widen the gap between the first bone 12 and the living tissue by the dilator 52 without using an additional instrument. While the gap is being thus widened, the bone and the living tissue can be treated. This can considerably improve convenience for the doctor at the time of a surgical operation. Also, there is no need for an additional instrument to widen the gap between the first bone 12 and the living tissue, so us it is not necessary to cut, for example, the skin of the patient to put through the instrument, and a burden on the patient can be reduced.

Although the sheath 33 described in the present embodiment has a circular cross sectional shape, it is also preferable that the sheath 33 has an elliptic cross sectional shape as has been described in the first embodiment. That is, it is also preferable to use the sheath 33 described in the first embodiment for the sheath 33 in the present embodiment.

The present invention is not limited to the embodiments described above, and various modifications can be made without departing from the spirit thereof. It is naturally possible to combine the treatment systems 11 according to the respective embodiments described above into one treatment system 11.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Other inventions which enable the embodiments described above are additionally noted below.

[1]

A surgical method using a probe unit, the probe unit comprising
a probe configured to treat a bone by ultrasonic vibration, and
a hollow sheath which surrounds the probe and which has a first portion at a small distance from a central axis, and a second portion at a greater distance from the central axis than the first portion,
the surgical method comprising:
inserting the sheath between the bone and a living tissue facing the bone so that the first portion is located between the bone and the living tissue; and
rotating the sheath between the bone and the living tissue so that the second portion is located between the bone and the living tissue, and treating the bone by the probe in this state.

[2]

A surgical method using a probe unit, the probe unit comprising
a probe configured to treat a bone by ultrasonic vibration,
a hollow sheath which surrounds the probe, and
an inflation member which intervenes between the sheath and the bone,
the surgical method comprising:
inserting the sheath between the bone and a living tissue; and
inflating the inflation member to widen the gap between the bone and the living tissue, and treating the bone by the probe in this state.

[3]

A surgical method using a probe unit, the probe unit comprising
a probe configured to treat a bone by ultrasonic vibration,
a hollow sheath which surrounds the probe, and
a linear dilator movable between a first position to be housed in the sheath and a second position to protrude from the sheath,
the surgical method comprising:
locating the sheath in the vicinity of the bone and a living tissue facing the bone; and
then locating the dilator at the second position to widen the gap between the bone and the living tissue facing the bone, and treating the bone by the probe in this state.

REFERENCE SIGNS LIST

11: treatment system, 12: bone, 13: second bone, 24: treatment instrument, 25: power supply unit, 26: probe, 27: vibrator unit, 28: grip portion, 31: probe unit, 33: sheath, 33A: insertion hole, 44: tapered portion, 44A: body portion, 45: knob, S: short diameter, L: long diameter, P1: first position, P2: second position, 46: groove, 47: bulge, 48: living tissue protection member, 51: inflation member, 52: dilator, 53: synovium.

What is claimed is:

1. A probe unit comprising:
a probe configured to treat a bone by ultrasonic vibration;
a hollow sheath surrounding the probe, the sheath including:
a first portion disposed at a small distance from a central axis of the sheath and having a short diameter,
a second portion disposed at a greater distance from the central axis than the first portion and having a long diameter such that the long diameter of the second portion intersects the short diameter of the first portion at right angles, and
a tapered portion provided on a distal side of the sheath, the tapered portion being smaller in diameter as the distance to a distal end of the sheath decreases; and
a knob having a diameter larger than that of the sheath, the knob being configured to rotate the sheath relative to the probe between: (i) a first position for insertion between the bone and the living tissue facing the bone so that the first portion is located between the bone and the living tissue, and (ii) a second position for insertion between the bone and the living tissue so that the second portion is located between the bone and the living tissue, wherein:
the length of the tapered portion along a longitudinal axis direction of the probe is greater than the diameter at a distal end of the tapered portion, and
a surface of the tapered portion is curved to become parallel to the longitudinal axis of the probe as the distance to the distal end of the sheath decreases.

2. A probe unit comprising:
a probe configured to treat a bone by ultrasonic vibration;
a hollow sheath surrounding the probe, the sheath including:
a first portion disposed at a small distance from a central axis of the sheath and having a short diameter,
a second portion disposed at a greater distance from the central axis than the first portion and having a long diameter such that the long diameter of the second portion intersects the short diameter of the first portion at right angles, and
a tapered portion provided on a distal side of the sheath, the tapered portion being smaller in diameter as the distance to a distal end of the sheath decreases; and
a knob configured to rotate the sheath relative to the probe between: (i) a first position for insertion between the bone and a living tissue facing the bone so that the first portion is located between the bone and the living tissue, and (ii) a second position for insertion between the bone and the living tissue so that the second portion is located between the bone and the living tissue, wherein:

the tapered portion has a groove, and the groove extends in a direction that intersects with a longitudinal axis direction of the probe.

3. A probe unit comprising:

a probe configured to treat a bone by ultrasonic vibration;

a hollow sheath surrounding the probe, the sheath including:
- a first portion disposed at a small distance from a central axis of the sheath and having a short diameter,
- a second portion disposed at a greater distance from the central axis than the first portion and having a long diameter such that the long diameter of the second portion intersects the short diameter of the first portion at right angles, and
- a tapered portion provided on a distal side of the sheath, the tapered portion being smaller in diameter as the distance to a distal end of the sheath decreases; and a knob configured to rotate the sheath relative to the probe between: (i) a first position for insertion between the bone and a living tissue facing the bone so that the first portion is located between the bone and the living tissue, and (ii) a second position for insertion between the bone and the living tissue so that the second portion is located between the bone and the living tissue, wherein:

the tapered portion has a groove, and the groove radially extends around a longitudinal axis of the probe.

* * * * *